US009523668B2

(12) United States Patent
Maruta et al.

(10) Patent No.: US 9,523,668 B2
(45) Date of Patent: Dec. 20, 2016

(54) FUEL PROPERTY DETERMINATION METHOD AND FUEL PROPERTY DETERMINATION DEVICE

(75) Inventors: Kaoru Maruta, Sendai (JP); Hisashi Nakamura, Sendai (JP); Soichiro Kato, Yokohama (JP)

(73) Assignees: TOHOKU UNIVERSITY (JP); IHI CORPORATION (JP)

( * ) Notice: Subject to any disclaimer, the term of this patent is extended or adjusted under 35 U.S.C. 154(b) by 480 days.

(21) Appl. No.: 13/522,357

(22) PCT Filed: May 18, 2010

(86) PCT No.: PCT/JP2010/003353
§ 371 (c)(1),
(2), (4) Date: Jul. 16, 2012

(87) PCT Pub. No.: WO2011/089659
PCT Pub. Date: Jul. 28, 2011

(65) Prior Publication Data
US 2012/0295365 A1    Nov. 22, 2012

(30) Foreign Application Priority Data
Jan. 19, 2010   (JP) ............... P2010-009369

(51) Int. Cl.
*G01N 31/12* (2006.01)
*G01N 33/28* (2006.01)
*G01N 1/22* (2006.01)

(52) U.S. Cl.
CPC ............ *G01N 33/2829* (2013.01); *G01N 1/22* (2013.01); *G01N 31/12* (2013.01)

(58) Field of Classification Search
CPC ................. G01N 31/12; G01N 1/22
(Continued)

(56) References Cited

U.S. PATENT DOCUMENTS 4,928,605 A    5/1990 Suwa et al.
4,968,402 A    11/1990 Kirker et al. ........... 208/68
(Continued)

FOREIGN PATENT DOCUMENTS

CA        1185811      4/1985
CN        101416053 A  4/2009
(Continued)

OTHER PUBLICATIONS

Catalytic Combustion in Microchannel for MEMS Power Generation Kaoru Maruta and Koichi Takeda Third Asia-Pacific Conference on Combustion Jun. 24-27, 2001.*
(Continued)

*Primary Examiner* — Krishnan S Menon
*Assistant Examiner* — Dwan A Gerido
(74) *Attorney, Agent, or Firm* — Ostrolenk Faber LLP

(57) ABSTRACT

A fuel property determination method includes a reaction mechanism analysis process (S1) of analyzing elementary reactions that compose chemical reactions between a plurality of types of initial materials including the materials that compose the fuel and obtaining the elementary reactions as fuel elementary reactions, and an octane number determination process (S2) of calculating the combustion characteristics of the fuel by performing a simulation based on the fuel elementary reactions and determining the octane number based on the combustion characteristics of the fuel.

12 Claims, 8 Drawing Sheets

(58) Field of Classification Search
USPC .......................................... 436/155; 422/78
See application file for complete search history.

(56) References Cited

U.S. PATENT DOCUMENTS

| | | | |
|---|---|---|---|
| 4,976,241 A | 12/1990 | Ishida et al. ................. | 123/425 |
| 2004/0220720 A1* | 11/2004 | Noda ............................ | 701/111 |
| 2008/0201084 A1* | 8/2008 | Lutnick et al. ................ | 702/23 |
| 2009/0151236 A1* | 6/2009 | Shibata ......................... | 44/447 |
| 2012/0006316 A1 | 1/2012 | Shimek | |

FOREIGN PATENT DOCUMENTS

| | | |
|---|---|---|
| DE | 3730046 A1 | 3/1989 |
| EP | 0 318 125 A2 | 5/1989 |
| JP | 2-216439 | 8/1990 |
| JP | 3-269353 | 11/1991 |
| JP | 07-257498 | 10/1995 |
| JP | 10-38470 | 2/1998 |
| JP | 10-142220 | 5/1998 |
| JP | 2004-332584 | 11/2004 |
| JP | 2010-112892 | 5/2010 |
| JP | 2010-216916 | 9/2010 |
| JP | 5051659 | 10/2012 |
| JP | 5224118 | 7/2013 |
| KR | 10-1990-0008355 | 6/1990 |
| KR | 10-1991-0017262 | 11/1991 |
| KR | 10-1996-0038373 | 11/1996 |
| RU | 2148826 C1 | 5/2000 |
| RU | 2149880 C1 | 5/2000 |
| RU | 2175131 C1 | 10/2001 |
| RU | 2274851 C2 | 4/2006 |
| RU | 2345359 C2 | 1/2009 |
| RU | 2349573 C2 | 3/2009 |
| SU | 545829 | 3/1977 |
| SU | 1695205 A1 | 11/1991 |
| SU | 1813095 A3 | 4/1993 |
| WO | 2009/110509 | 9/2009 |

OTHER PUBLICATIONS

Russian Decision on Grant, dated Aug. 4, 2014, issued in corresponding Russian Patent Application No. 2013126881/28(039921), date filed Nov. 18, 2011. English Translation. Total 10 pages.

Search Report dated Aug. 17, 2010 issued in corresponding International Patent Application No. PCT/JP2010/003353 with English translation.

Search Report dated Jan. 10, 2012 issued in corresponding International Patent Application No. PCT/JP2011/076681 with English translation.

Jis K 2280-1996 Petroleum Products-Fuels-Determination of Octane Number, Cetane Number and Calculation of Cetane Index (1996) pp. 1084-1149 with partial English translation.

Hisashi Nakamura et al. "Ondo Bunpu Seigyogata Micro Flow Reactor o Mochiita PRF no Jichakka Tokusei" , Proceedings of the Japanese symposium on Combustion (2009) Dai 47 Kai, pp. 234-235.

Standard Method of Test for Autoignition Temperature of Liquid Petroleum Products, American Society for Testing and Materials D2155-66 (1976) pp. 711-714.

Standard Test Method for Autoignition Temperature of Liquid Chemicals, American Society for Testing and Materials E659-78 (2005) pp. 1-6.

Hiroshi Oshibe, et al., "Study on combustion characteristic of DME in micro flowreactor with temperature control", National Heat Transfer Symposium of Japan Koen Ronbunshu (CD-ROM) (2008) vol. 45, p. D1510 (with English Abstract).

Korean Office Action. dated Jun. 18, 2014, issued in corresponding to Korean Patent Application No. 10-2013-7012410. English translation, Total 9 pages.

Chinese Office Action, dated Jun. 24, 2014, issued in corresponding to Chinese Patent Application No. 201180055191.6, English translation, Total 8 page Chinese Office Action dated Feb. 11, 2014 issued in corresponding Chinese Patent Application No. 201080061650.7 with English translation.

T. Tsurushima "A new skeletal PRF kinetic model for HCCI combustion", Proceedings of the Combustion Institute (2009), vol. 32, issue 2, pp. 2835-2841.

Kaoru Maruta et al. "Catalytic Combustion in Microchannel for MEMS Power Generation", The Third Asia-Pacific Conference on Combustion, (2001).

Gunther Kolb et al., "A micro-structured 5kW complete fuel processor for iso-octane as hydrogen supply system for, mobile auxiliary power units Part II—Development of water-gas shift and preferential oxidation catalysts reactors and assembly of the fuel processor", Chemical-Engineering Journal (2008), vol. 138, pp. 474-489.

Wang Zhi et al. "Study of HCCI Combustion Characteristics with High RON Fuel", Transactions of CSICE (2004), vol. 22, No. 1 (English abstract on first page).

Kaoru Maruta et al., "Lower limit of weak flame in a heated channel", Proceedings of the Combustion Institute (2009), vol. 32, pp. 3075-3081.

Office Action dated Nov. 13, 2013 issued in corresponding Korean Patent Application No. 10-2012-7019755 with English translation.

Office Action dated Nov. 26, 2013 issued in corresponding Russian Patent Application No. 2012134647 with English translation.

Russian Office Action, dated Apr. 18, 2014, issued in corresponding Russian Patent Application No. 2013126881/28(039921). English Translation attached. Total 11 pages.

Russian Office Action, dated May 23, 2014, issued in corresponding Russian Patent Application No. 2012134647/15(055371). English Translation attached. Total 13 pages.

Decision on Refusal dated Jun. 3, 2015 issued in corresponding Russian Patent Application No. 2012134647 with English translation.

Search Report dated Jul. 14, 2015 issued in corresponding European Patent Application No. 10843-825.0.

T. Ogura et al., "Modeling of the Oxidation of Primary Reference Fuel in the Presence of Oxygenated Octane Improvers: Ethyl Tert-Butyl Ether and Ethanol", Energy & Fuels, vol. 21, No. 6 (2007) pp. 3233-3239.

R.F. Cracknell et al., "The chemical origin of octane sensitivity in gasoline fuels containing nitroalkanes", Combustion and Flame Elsevier Science Publishing Co., Inc., vol. 156, No. 5, (2008) pp. 1046-1052.

L.J. Kirsch et al., "A Fundamentally Based Model of Knock in the Gasoline Engine", Symposium (International) on Combustion, vol. 16, (1976) pp. 233-244.

Cengel, Yunus, "Heat Transfer a Practical Approach," McGraw Hill, New York, New York, 2003, p. 682.

Hiroshi Oshibe, et al. "Stabilized three-stage oxidation of DME/air mixture in a micro flow reactor with a controlled temperature profile", Combustion and Flame, vol. 157, Apr. 9, 2010.

Akira Yamamoto, et al., "Stabilized three-stage oxidation of gaseous $n$-heptane/air mixture in a micro flow reactor with a controlled temperature profile," Proceedings of the Combustion Institute, vol. 33, No. 2, Aug. 7, 2010, pp. 3259-3266.

* cited by examiner

FUEL PROPERTY DETERMINATION METHOD AND FUEL PROPERTY DETERMINATION DEVICE

CROSS-REFERENCE TO RELATED APPLICATIONS

The present application is a 35 U.S.C. §§371 national phase conversion of PCT/JP2010/003353, filed May 18, 2010, which claims priority of Japanese Patent Application No. 2010-009369, filed Jan. 19, 2010, the contents of which are incorporated herein by reference. The PCT International Application was published in the Japanese language.

TECHNICAL FIELD

BACKGROUND ART

One of values that represent the property of a fuel is the octane number, which is an index that represents the knock resistance of a fuel. The octane number is 100 for isooctane that has high knock resistance and 0 for n-heptane that has low knock resistance. Furthermore, the octane number of a fuel is a value that corresponds to the % volume of isooctane in a mixed fuel (reference fuel) of isooctane and n-heptane with the same knock resistance. That is, in a case where the knock resistance of a fuel is the same as that of the mixed fuel described above in which the mixing ratio of isooctane is a volume ratio of 50%, the octane number of the fuel is indicated as 50.

Incidentally, there are a variety of types of octane numbers according to the determination technique thereof or the like. Typical examples include the research method octane number that is adopted as an index in countries such as Japan, and the motor method octane number that is adopted as an index in countries such as Germany.

Furthermore, when determining the octane number of an unknown fuel, the octane number is determined by conducting experiments in accordance with the determination techniques described above.

Specifically, in the research method octane number and the motor method octane number, a CFR engine that is specifically designed to measure the octane number is driven by the fuel described above. The octane number is then determined by comparing the pressure fluctuation characteristics of the combustion chamber of a case where the engine is driven by the unknown fuel with a case where the engine is driven by the reference fuel.

The pressure value of the combustion chamber of an internal combustion engine is changed by knocking. The presence of knocking is therefore measured by measuring the pressure value of the combustion chamber. Furthermore, the octane number described above is determined by comparing the measurement timings and the measurement values of the fuel that is the measurement target with those of the reference fuel.

CITATION LIST

Non-Patent Document

[NPL 1] JIS (Japanese Industrial Standards) K2280

SUMMARY OF INVENTION

Technical Problem

However, the pressure value of the combustion chamber varies according to the degree of dirt in the combustion chamber of the CFR engine. Therefore, in order to determine an accurate octane number, it is necessary to conduct a preliminary experiment for ascertaining the degree of dirt in the combustion chamber prior to an experiment for determining the octane number of the fuel.

For example, in a case where the research method octane number is to be determined, a preliminary experiment is conducted in which the CFR engine is operated using a toluene type inspection fuel and the degree of dirt in the combustion chamber is ascertained from the operation state.

Furthermore, it is necessary to conduct an experiment for determining the octane number by taking into account of the degree of dirt in the combustion chamber which is ascertained by the preliminary experiment.

That is, with the octane number determination method of the related art, it is necessary to perform the preliminary experiment described above every time an experiment to determine the octane number is conducted, which is a complex process.

Here, in the related art, without being limited to the research method octane number or the motor method octane number, in a case where the octane number is to be determined, the internal combustion engine is actually operated using the target fuel and the reference fuel, and the octane number is determined from the operation state. Therefore, since the measurement value changes according to the condition of the combustion chamber of the internal combustion engine and the like, it is difficult to determine an accurate octane number.

Further, with the octane number determination method of the related art, in a case where an octane number according to the actual usage environment of the internal combustion engine is to be determined, it is necessary to determine the octane number by actually recreating such an environment each time and conducting the experiment described above therein. For example, in a case where an octane number according to the temperature of the fuel is to be determined, it is necessary to conduct an experiment by actually changing the temperature of the fuel.

Therefore, with the octane number determination method of the related art, it is necessary to prepare an internal combustion engine each time, to arrange a facility for forming the environment, and to perform many large-scale experiments. The process is therefore complex.

The present invention is conceived in view of the problems described above, and an object thereof is to determine the property (octane number or the like) of a fuel more easily.

Solution to Problem

The present invention adopts the configurations described below as a solution to the problem described above.

A first invention is a fuel property determination method of determining a property of a fuel, including: a reaction mechanism analysis process of analyzing elementary reactions that compose chemical reactions between a plurality of types of initial materials including materials that compose the fuel and obtaining the elementary reactions as fuel elementary reactions; and a property determination process of calculating combustion characteristics of the fuel by performing a simulation based on the fuel elementary reactions and determining a property of the fuel based on the combustion characteristics of the fuel.

In a second invention, according to the first invention described above, the property of the fuel may be an octane number, and the property determination process may be an octane number determination process of determining the octane number of the fuel.

In a third invention, according to the second invention described above, the reaction mechanism analysis process may perform: a calculation process of calculating simulation data using elementary reaction data including a plurality of elementary reaction formulae that describe the chemical reactions and parameters that are associated with the elementary reaction formulae, and computation data including equations that are time-one-dimensionalized in zero-dimensional space for calculating the simulation data from the elementary reaction data; a determination process of determining whether or not experiment data including a one-dimensional space temperature distribution at a time of the chemical reactions which is obtained by an experiment can be derived from the simulation data; and a parameter adjustment process of adjusting the parameters that are included in the elementary reaction data, and the parameter adjustment process and the calculation process using the adjusted parameters may be repeatedly performed until it is determined in the determination process that the experiment data can be derived from the simulation data.

In a fourth invention, according to the second or third invention described above, in the octane number determination process, the octane number may be determined by comparing the combustion characteristics of the fuel with combustion characteristics of a reference fuel including a composition that is regulated in advance.

In a fifth invention, according to the fourth invention described above, in the reaction mechanism analysis process, elementary reactions that compose chemical reactions between a plurality of types of initial materials including materials that compose the reference fuel may be analyzed and obtained as reference fuel elementary reactions, and in the octane number determination process, the combustion characteristics of the reference fuel may be calculated by performing a simulation based on the reference fuel elementary reactions.

In a sixth invention, according to any one of the second to fifth inventions described above, the octane number may be determined based on at least one of a calorific values of a cool flame and a hot flame that are generated when the fuel is combusted, a ratio of the calorific value of the cool flame and the calorific value of the hot flame that are generated when the fuel is combusted, and ignition temperatures of the cool flame and the hot flame that are generated when the fuel is combusted, which are types of the combustion characteristics of the fuel.

A seventh invention is a fuel property determination device that determines a property of a fuel, including: reaction mechanism analysis means that analyzes elementary reactions that compose chemical reactions between a plurality of types of initial materials including materials that compose the fuel and obtains the elementary reactions as fuel elementary reactions; and property determination means that calculates combustion characteristics of the fuel by performing a simulation based on the fuel elementary reactions and determines a property of the fuel based on the combustion characteristics of the fuel.

In an eighth invention, according to the seventh invention described above, the property of the fuel may be an octane number, and the property determination means may be octane number determination means that determines the octane number of the fuel.

In a ninth invention, according to the eighth invention described above, the reaction mechanism analysis means may include: experiment data storage means that stores, as experiment data, a one-dimensional space temperature distribution at a time of the chemical reactions, the one-dimensional space temperature distribution being obtained by an experiment; elementary reaction data storage means that stores, as elementary reaction data, a plurality of elementary reaction formulae that describe the chemical reactions and parameters that are associated with the elementary reaction formulae; computation data storage means that stores, as computation data, equations that are time-one-dimensionalized in zero-dimensional space for calculating simulation data from the elementary reaction data; calculation means that calculates the simulation data using the elementary reaction data and the equations that are time-one-dimensionalized in zero-dimensional space; determination means that determines whether or not the experiment data can be derived from the simulation data; parameter adjustment means that adjusts the parameters that are included in the elementary reaction data; and control means that repeatedly executes an adjustment of the parameters by the parameter adjustment means and a calculation of the simulation data using the adjusted parameters by the calculation means until the determination means determines that the experiment data can be derived from the simulation data.

In a tenth invention, according to the eighth or ninth invention described above, the octane number determination may determine the octane number by comparing the combustion characteristics of the fuel with combustion characteristics of a reference fuel including a composition that is regulated in advance.

In an eleventh invention, according to the tenth invention described above, the reaction mechanism analysis means may analyze elementary reactions that compose chemical reactions between a plurality of types of initial materials including materials that compose the reference fuel and obtains the elementary reactions as reference fuel elementary reactions, and the octane number determination means may calculate the combustion characteristics of the reference fuel by performing a simulation based on the reference fuel elementary reactions.

In a twelfth invention, according to the eighth to eleventh inventions described above, the octane number determination means may determine the octane number based on at least one of calorific values of a cool flame and a hot flame that are generated when the fuel is combusted, a ratio of the calorific value of the cool flame and the calorific value of the hot flame that are generated when the fuel is combusted, and ignition temperatures of the cool flame and the hot flame that are generated when the fuel is combusted, which are types of the combustion characteristics of the fuel.

Advantageous Effects of Invention

According to the present invention, the elementary reactions that compose the chemical reactions at the time of the combustion of the materials that compose the target fuel are analyzed. Furthermore, the combustion characteristics of the target fuel are calculated by performing a simulation based on the analysis result. Furthermore, property (octane number) is determined based on the combustion characteristics.

That is, according to the present invention, it is possible to determine property (octane number) without performing an experiment using an internal combustion engine which was performed in the related art when determining property (octane number).

Therefore, according to the present invention, the property (octane number) of a fuel can be determined more easily.

DESCRIPTION OF EMBODIMENTS

Embodiments of the fuel property determination method and the fuel property determination device according to the present invention will be described below with reference to the drawings.

(First Embodiment)

The fuel property determination method and the fuel property determination device of the present embodiment determine the octane number (property) of a fuel for which the octane number is unknown (hereinafter referred to as an unknown fuel) by analyzing the elementary reactions of a combustion reaction of the unknown fuel and performing a simulation based on the elementary reactions.

Here, in order to determine the octane number more accurately, it is necessary to execute an accurate simulation based on actual phenomena. It is therefore necessary to obtain elementary reaction data for executing an accurate simulation. Further, realistically, it is necessary to obtain the elementary reaction data in as short a period of time as possible.

Therefore, in order to satisfy such requirements, the fuel property determination method and the fuel property determination device of the present embodiment compare a one-dimensional space temperature distribution (experiment data) that is obtained using a microflow reactor (experiment device) described later with simulation data that is obtained using elementary reaction formulae, parameters that are associated with the elementary reaction formulae, and equations that are time-one-dimensionalized in zero-dimensional space. Furthermore, the fuel property determination method and the fuel property determination device of the present embodiment perform full chemistry analysis of the combustion reaction (chemical reactions) between the unknown fuel and oxygen using an elementary reaction analysis technique of obtaining the solution to the parameters by performing a convergence calculation while adjusting the parameters until the experiment data can be derived from the simulation data.

Furthermore, similarly to the unknown fuel, the fuel property determination method and the fuel property determination device of the present embodiment also perform full chemistry analysis of a reference fuel (a mixed fuel of isooctane and n-heptane, a fuel formed only of isooctane, or a fuel formed only of n-heptane).

First, the microflow reactor of the present embodiment which is used to obtain experiment data for performing an accurate simulation and a method of obtaining a one-dimensional space temperature distribution using the microflow reactor will be described.

Figure 1:
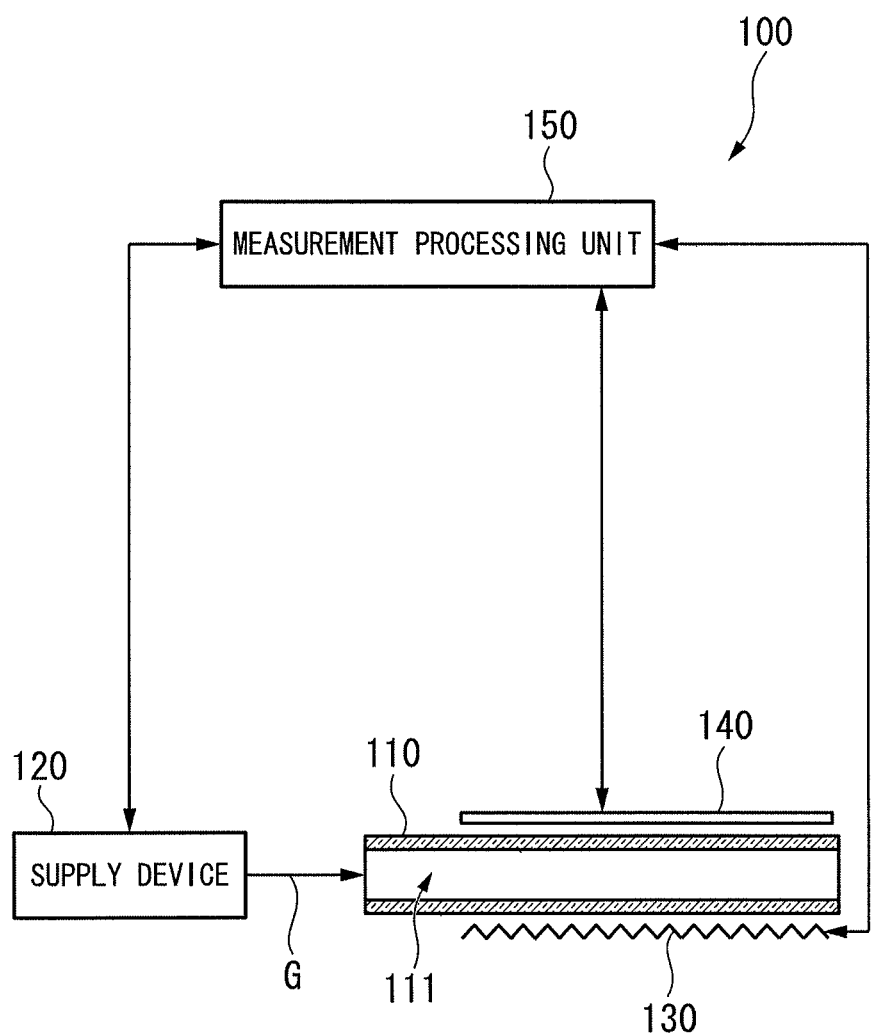
FIG. 1 is a schematic view that illustrates an outline configuration of a microflow reactor for obtaining experiment data that is used by a fuel property determination method and a fuel property determination device according to a first embodiment of the present invention.

FIG. 1 is a schematic view that illustrates an outline configuration of a microflow reactor 100. As illustrated in the drawing, the microflow reactor 100 includes a pipe 110, a supply device 120, a heater 130, a temperature measuring device 140, and a measurement processing unit 150.

The pipe 110 is a cylindrical straight pipe. Furthermore, the diameter of an inner flow path 111 of the pipe 110 is set to be smaller than the extinguishing distance that is the threshold value at which a flame that is formed in the inner flow path 111 is extinguished without being spread at room temperature. That is, the inner flow path 111 of the pipe 110 is set to have a smaller diameter than the extinguishing diameter at room temperature.

The supply device 120 is a member that supplies a premixed gas G, in which a fuel (unknown fuel or reference fuel) that is the initial material to be combusted and an oxidant (for example, oxygen or air) are mixed, to the pipe 110. Furthermore, the supply device 120 supplies the premixed gas G to the pipe 110 by causing the premixed gas G to flow into the inner supply path 111 of the pipe 110 from one end of the pipe 110.

The supply device 120 can adjust the flow amount of the premixed gas G that is supplied to the pipe 110. Therefore, the supply device 120 continuously reduces the flow amount of the premixed gas G that is supplied to the pipe 110 so that the flow amount thereof satisfies the conditions that the flame formed in the inner flow path 111 of the pipe 110 is stable and that the formation position of the flame is not influenced by the flow speed of the premixed gas G. Here, the flow amount that satisfies the conditions that the flame that is formed in the inner flow path 111 of the pipe 110 is stable and that the formation position of the flame is not influenced by the flow speed of the premixed gas G will be described in detail later.

Further, the supply device 120 is electrically connected to the measurement processing unit 150. The supply device 120 can therefore adjust the flow amount, temperature, pressure, and the like of the premixed gas G, and the ratio of the fuel and the oxidant in the premixed gas G (that is, the initial concentration of the fuel and the oxidant) based on an instruction from the measurement processing unit 150.

The heater 130 is a member that heats the pipe 110. Furthermore, the heater 130 heats the pipe 110 so that the temperature of the inner flow path 111 continuously rises from room temperature in the flow direction of the premixed gas G until the temperature of the inner flow path 111 in a middle portion becomes equal to or greater than the assumed ignition temperature of the premixed gas G.

The temperature measuring device 140 is a member that measures the gas temperature in the inner flow path 111 of the pipe 110. The temperature measuring device 140 is electrically connected to the measurement processing unit 150, and inputs the measurement result into the measurement processing unit 150.

The measurement processing unit 150 is a member that obtains the temperature distribution by causing the measurement result that is input from the temperature measuring device 140 to correspond with the positions in the pipe 110 and storing the measurement result. Further, the measurement processing unit 150 stores experiment conditions such as the flow amount and temperature of the premixed gas G that is supplied from the supply device 120 to the pipe 110, the types of the fuel and oxidant that are included in the premixed gas G, and the initial concentrations of the fuel and the oxidant.

Next, an experiment method of obtaining a one-dimensional space temperature distribution using the above-described microflow reactor 100 (hereinafter referred to as a main experiment) will be described.

The premixed gas G in which the fuel and the oxidant are mixed at a predetermined initial concentration is supplied from the supply device 120 to the inner flow path 111 of the pipe 110.

The pipe 110 is heated so that the temperature of the inner flow path 111 becomes equal to or greater than the ignition temperature of the premixed gas G. Therefore, the premixed gas G that is supplied to the inner flow path 111 of the pipe 110 is heated from one end portion toward the other end portion of the inner flow path 111 of the pipe 110. Furthermore, the premixed gas G is ignited at a point when the premixed gas G is heated to equal to or greater than the ignition temperature.

The flame that is formed by the ignition of the premixed gas G trembles in a case where the flow speed of the premixed gas G in the inner flow path 111 of the pipe 110 is fast. Such a phenomenon is due to repeated ignition and extinguishing of the premixed gas G in a short period of time.

On the other hand, in a case where the flow speed of the premixed gas G in the inner flow path 111 of the pipe 110 is slow, the combustion state is continuously maintained, and the flame stabilizes.

Therefore, in the main experiment, first, the premixed gas G with a flow amount which makes the flow speed in the inner flow path 111 of the pipe 110 sufficiently fast is supplied to the pipe 110. The flow amount of the premixed gas G is then gradually reduced, and the flow amount of the premixed gas G is reduced until the flame stabilizes.

Here, the temperature of a mixed gas (a mixture of the present invention includes the meanings of both a gas formed only of a premixed gas and a gas in which a premixed gas and an intermediate product are mixed) in the inner flow path 111 rises rapidly at the position where the flame is formed. Therefore, in the main experiment, the position at which the temperature of the mixed gas in the inner flow path 111 rises rapidly is analyzed based on the measurement result that is input from the temperature measuring device 140. Furthermore, in the main experiment, the flame is stabilized by reducing the flow amount of the premixed gas G until the position described above no longer fluctuates.

Further, the pipe 110 may be formed using a material in which the inside is visible, and the flow amount of the premixed gas G may be reduced until the formation position of the flame stabilizes while checking the formation position of the flame using an imaging device or the like.

Here, when the flow amount of the premixed gas G is reduced until the flame stabilizes, the formation position of the flame is no longer influenced by the flow speed of the premixed gas G.

Figure 2:
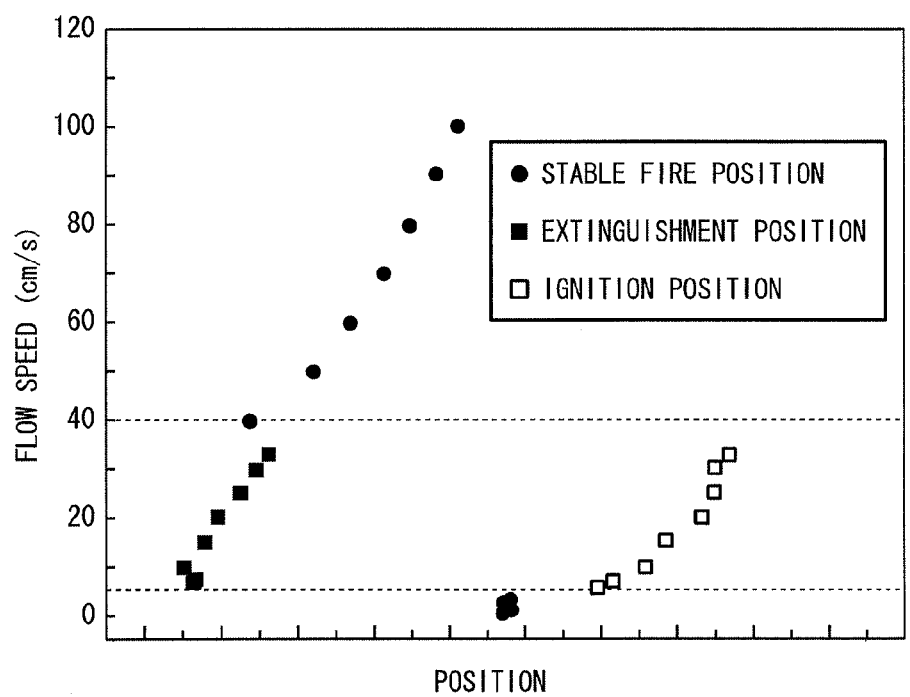
FIG. 2 is a graph for describing that in the microflow reactor illustrated in FIG. 1, the flame is stabilized and there is a flow amount that is not dependent on the flow speed of premixed gas that is supplied.

FIG. 2 is a graph that illustrates the relationship between the flow speed of the premixed gas G in the inner flow path 111 of the pipe 110 and the position at which the flame stabilizes, the ignition position, and the extinguishing position. Here, the graph illustrated in FIG. 2 is based on data that is obtained by supplying a premixed gas G with a stoichiometric ratio of methane and air to a pipe 110 with a diameter of 2 mm.

As illustrated in the drawing, it can be seen that while the flame stabilizes in a case where the flow speed of the premixed gas G is fast (40 to 100 cm/s), the formation position of the flame is influenced by the flow speed. Further, it can be seen that in a case where the flow speed of the premixed gas G is slower (5 to 40 cm/s) than the flow speed described above, the flame trembles. Furthermore, it can be seen that in a case where the flow speed of the premixed gas G is even slower (0.2 to 5 cm/s) than the flow speed described above, the flame stabilizes and the formation position of the flame is not influenced by the flow speed. In such a manner, the state of the flame changes according to the flow speed of the premixed gas G in the inner flow path 111 of the pipe 110.

Furthermore, in the main experiment, the flow amount of the premixed gas G is set so that the flow speed of the premixed gas G becomes a flow speed with which the flame stabilizes and the formation position of the flame is not influenced by the flow speed.

After the flame stabilizes so that the formation position is not dependent on the flow speed of the premixed gas G in such a manner, the measurement processing unit 150 obtains and outputs the temperature distribution.

Furthermore, in the main experiment, a combustion reaction takes place in the inner flow path 111 of the pipe 110 which is an extremely long and thin straight pipe in which the inner flow path 111 has a diameter that is set to be smaller than the extinguishing diameter at room temperature. Therefore, unlike an experiment space that expands three-dimensionally, the experiment space in the main experiment expands only in the flow direction. Therefore, the temperature distribution that is obtained as the experiment result of the main experiment can be considered to be temperature changes in one-dimensional space.

Further, in the main experiment, the formation position of the flame is not dependent on the flow speed of the premixed gas G, and the inner flow path 111 is heat-regulated from the outside by the heating of the pipe 110 by the heater 130. Therefore, the influence due to the transfer of heat in the inner flow path 111 is clear. Furthermore, the flow speed of the premixed gas G is low and the amount of input heat is sufficiently small compared with the heat capacity of the pipe 110. Temperature changes in the pipe 110 due to the combustion reaction can therefore be ignored. Therefore, in the main experiment, the temperature distribution can be obtained by removing the influence of uncertain variables in the experiment environment.

In such a manner, in the main experiment, a one-dimensional space temperature distribution from which the influence of uncertain variables in the experiment environment is removed can be obtained.

Next, the fuel property determination method and the fuel property determination device of the present embodiment will be described.

Figure 3:
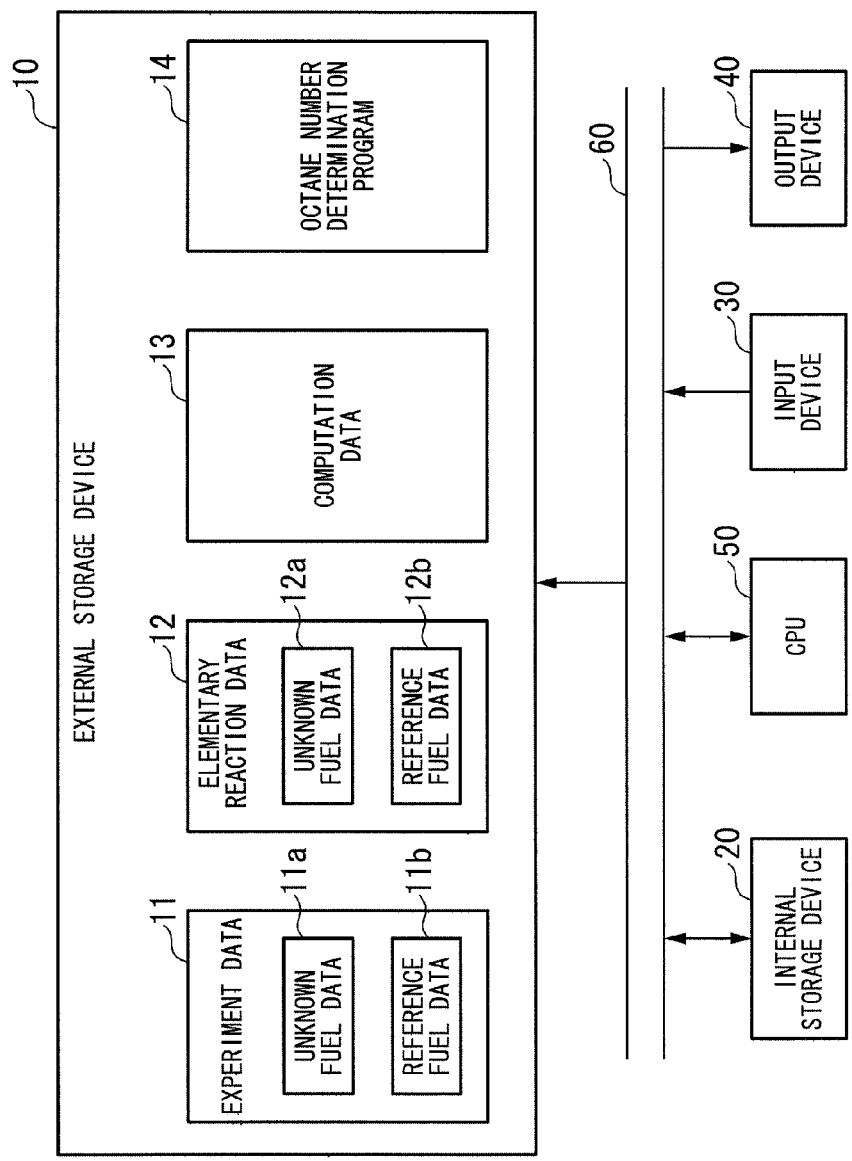
FIG. 3 is a block diagram that illustrates the hardware configuration of the fuel property determination device according to the first embodiment of the present invention.

FIG. 3 is a block diagram that illustrates the hardware configuration of the fuel property determination device of the present embodiment. A fuel property determination device A1 of the present embodiment is a device that is realized by a computer such as, for example, a work station or a super computer. Furthermore, as illustrated in FIG. 3, the fuel property determination device A1 of the present embodiment includes an external storage device 10, an internal storage device 20, an input device 30, an output device 40, and a CPU (Central Processing Unit) 50.

Here, the external storage device 10, the internal storage device 20, the input device 30, the output device 40, and the CPU 50 are connected to each other by a system bus 60.

The external storage device 10 is a device that stores various pieces of data, programs, and the like that are used in the computation process of the CPU 50. In the present embodiment, the external storage device 10 stores experiment data 11, elementary reaction data 12, computation data 13, and an octane number determination program 14.

Furthermore, as such an external storage device 10, for example, a hard disk device or a removable medium device may be used. Here, the experiment data 11, the elementary reaction data 12, the computation data 13, and the octane number determination program 14 are stored on a removable medium such as an optical disc or a memory in advance. The experiment data 11, the elementary reaction data 12, the computation data 13, and the octane number determination program 14 may be stored in the external storage device 10 by connecting the removable disk as a configuration of the external storage device 10 to a reaction mechanism analysis device. Further, the experiment data 11, the elementary reaction data 12, the computation data 13, and the octane number determination program 14 may be stored on a hard disk as a configuration of the external storage device 10 by downloading them from the removable disk via a network or being input via the input device 30.

The experiment data 11 includes experiment data and experiment conditions that are obtained by the microflow reactor 100 described above. In more detail, the experiment data 11 includes the one-dimensional space temperature distribution from which the influence of uncertain variables in the experiment environment is removed, the flow amount, temperature, pressure, and the like of the premixed gas G that is supplied from the supply device 120 to the pipe 110, the types of the fuel and the oxidant that are included in the premixed gas G, the initial concentration of the fuel and the oxidant, and the like.

Furthermore, as illustrated in FIG. 3, the experiment data 11 includes unknown fuel data 11a that is data that relates to the unknown fuel, and reference fuel data 11b that is data that relates to the reference fuel.

The elementary reaction data 12 is a database in which a plurality of elementary reaction formulae that describe the combustion reaction between the oxidant and the fuel (unknown fuel or reference fuel), the reaction mechanism of which is the target of analysis (that is, of performing full chemistry analysis) in the fuel property determination device A1 of the present embodiment, and parameters (for example, the frequency coefficient and the activation energy) that relate to the elementary reaction formulae are collected. Here, in the description below, the database will be referred to as an elementary reaction mechanism.

The elementary reaction mechanism can also use an existing mechanism. Further, in a case where there are no existing elementary reaction mechanisms, the elementary reaction mechanism can be obtained using a molecular dynamics method or the like.

Further, as illustrated in FIG. 3, the elementary reaction data 12 includes unknown fuel data 12a that is the elementary reaction mechanism that relates to the unknown fuel, and reference fuel data 12b that is the elementary reaction mechanism that relates to the reference fuel.

The computation data 13 includes Formulae 1 and 2 for the CPU 50 calculating changes in the concentration of intermediate products and changes in the temperature of a mixed gas based on the elementary reaction data 12 and the parameters that are input from the input device 30.

Further, the mixed gas referred to here is a gas in which unreacted premixed gas and intermediate products that are generated during the course of the combustion reaction are mixed.

[Formula 1]

$$\frac{dY_k}{dt} = v\dot{\omega}_k W_k \quad (1)$$

$Y_k$: mass fraction of chemical species k (intermediate product)
v: specific volume
t: time
$\dot{\omega}_k$: mole generation speed of chemical species k (intermediate product)
$W_k$: molecular weight of chemical species k (intermediate product)

[Formula 2]

$$c_p \frac{dT}{dt} + v\sum_{k}^{K} h_k \dot{\omega}_k W_k - v\frac{4\lambda Nu}{d^2}(T_w - T) = 0 \quad (2)$$

$c_p$: constant pressure specific heat
T: temperature of mixed gas
K: number of chemical species (intermediate products)
$h_k$: specific enthalpy of chemical species (intermediate product)
$\lambda$: thermal conductivity of mixed gas
Nu: Nusselt number
Tw: wall surface temperature Formula 1 is for the conservation of mass in time-one-dimensional constant pressure combustion in normal zero-dimensional space. Further, Formula 2 is a formula for energy conservation, wherein the first item on the left is an item that represents the inner energy of the mixed gas, the second item from the left is an item that represents the energy that is moved by the elementary reactions, and the third item from the left is an item that represents the energy that is moved by the heat transfer between the mixed gas and the outside (that is, the energy that is moved by the heat transfer between the mixed gas and the wall surface of the microflow reactor 100 (the inner face of the pipe 110)).

Changes in the concentration of the intermediate products and changes in the temperature of the mixed gas are calculated by a system of equations of Formulae 1 and 2. Here, Formulae 1 and 2 are time-one-dimensional equations in zero-dimensional space in which the independent variable is time, the dependent variables are concentration and temperature, and positions are not included in the parameters.

Furthermore, changes in the concentration of the intermediate products and changes in the temperature of the mixed gas are calculated by equations that are time-one-dimensionalized in zero-dimensional space in which the concept of space is not considered as described above.

Further, the computation data 13 includes Formulae 3 and 4 for space one-dimensionalizing the changes in the temperature of the mixed gas which are calculated using Formulae 1 and 2 described above.

Here, the heat capacity of the pipe 110 in the microflow reactor 100 is sufficiently greater than the calorific value of the premixed gas with a low flow rate. Changes in the pipe wall temperature distribution due to the flame can therefore be ignored. Therefore, the pipe wall temperature distribution is given as a function of the position in the pipe 110. Accordingly, the changes in the temperature of the mixed gas which are calculated using Formulae 1 and 2 described above can be space one-dimensionalized by Formulae 3 and 4.

[Formula 3]

$$U = U_0 \frac{T}{T_0} \quad (3)$$

U: movement speed (change in density of mixed gas)
$U_0$: supply speed of premixed gas
$T_0$: initial temperature of premixed gas
[Formula 4]

$$x = \int U dt \quad (4)$$

x: position

Here, the computation data 13 includes various calculation conditions that are necessary for a simulation that calculates the combustion characteristics.

The octane number determination program 14 is a program for causing the fuel property determination device A1 of the present embodiment to function as each of the functional configurations illustrated in FIG. 4 described later.

Here, the octane number determination program 14 will be described in detail together with the description of the functional configuration of the fuel property determination device A1 later with reference to FIG. 4.

The internal storage device 20 is a device that stores the operation program of the CPU 50, and temporarily stores various pieces of data and programs that are stored in the external storage device 10 and temporarily stores the computation result of the CPU 50 under the control of the CPU 50. A RAM (Random Access Memory), a ROM (Read Only Memory), or the like is used as the internal storage device 20.

The input device 30 is a device for external input of data to the fuel property determination device A1 of the present embodiment, and for example, a keyboard and a mouse are used. However, in a case where input of the data to the fuel property determination device A1 of the present embodiment is performed via a communication path, a communication device that is the interface with the communication path may be used as the input device 30.

The output device 40 is a device that outputs data that is stored in the external storage device 10 or the internal storage device 20 under the control of the CPU 50, and for example, a display or a printer for visualizing the data is used. However, in a case where output of the data from the fuel property determination device A1 of the present embodiment is performed via a communication path, a communication device that is an interface with the communication path may be used as the output device 40.

The CPU 50 is a device that controls the overall operation of the fuel property determination device A1 of the present embodiment. Furthermore, the CPU 50 in the fuel property determination device A1 of the present embodiment performs, based on the octane number determination program 14, calculation of changes in the concentration of intermediate products and changes in the temperature of a mixed gas, comparison and determination of the simulation data with the experiment data, adjustment of the parameters in the elementary reaction mechanism, simulation using the elementary reaction mechanism, determination of the octane number of an unknown fuel, and the like.

Figure 4:
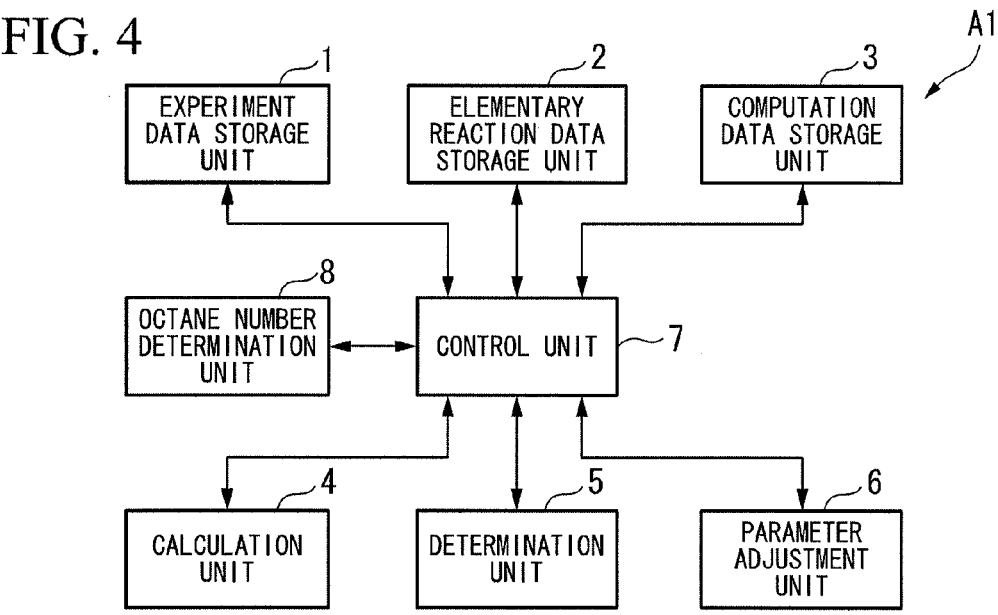
FIG. 4 is a block diagram that illustrates the functional configuration of the fuel property determination device according to the first embodiment of the present invention.

FIG. 4 is a block diagram that illustrates the functional configuration of the fuel property determination device A1 of the present embodiment. As illustrated in the drawing, according to the octane number determination program 14, the fuel property determination device A1 of the present embodiment includes the functions of an experiment data storage unit 1 (experiment data storage means), an elementary reaction data storage unit 2 (elementary reaction data storage means), a computation data storage unit 3 (computation data storage means), a calculation unit 4 (calculation means), a determination unit 5 (determination means), a parameter adjustment unit 6 (parameter adjustment means), a control unit 7 (control means), and an octane number determination unit 8 (octane number determination means).

Here, in the present embodiment, the reaction mechanism analysis means of the present invention is configured by the experiment data storage unit 1, the elementary reaction data storage unit 2, the computation data storage unit 3, the calculation unit 4, the determination unit 5, the parameter adjustment unit 6, and the control unit 7.

The experiment data storage unit 1 stores the experiment data 11. Further, the elementary reaction data storage unit 2 stores the elementary reaction data 12. Further, the computation data storage unit 3 stores the computation data 13.

Furthermore, the octane number determination program 14 causes the external storage device 10 that stores the experiment data 11, the elementary reaction data 12, and the computation data 13, or the internal storage device 20 to which the experiment data 11, the elementary reaction data 12, and the computation data 13 are moved, to function as the experiment data storage unit 1, the elementary reaction data storage unit 2, and the computation data storage unit 3.

The calculation unit 4 calculates changes in the concentration of the intermediate products and changes in the temperature of the mixed gas using Formulae 1 and 2 that are equations that are time-one-dimensionalized in zero-dimensional space and that are stored as the computation data 13 in the computation data storage unit 3, the experiment conditions that are included in the experiment data 11 that is stored in the experiment data storage unit 1, and the elementary reaction data 12 that is stored in the elementary reaction data storage unit 2.

Furthermore, the octane number determination program 14 causes the fuel property determination device A1 to function as the calculation unit 4 by causing the CPU 50 to calculate changes in the concentration of the intermediate products and changes in the temperature of the mixed gas based on the experiment data 11, the elementary reaction data 12, and the computation data 13 that are stored in the external storage device 10 or the internal storage device 20.

The determination unit 5 compares the changes in the temperature of the mixed gas (simulation data) which are calculated by the calculation unit 4 with the experiment data 11. Furthermore, the determination unit 5 performs determination of whether or not the temperature distribution that is included in the experiment data 11 (gas temperature distribution in the inner flow path 111) can be derived from the changes in the temperature of the mixed gas which are calculated by the calculation unit 4.

Specifically, the determination unit 5 calculates the simulation temperature distribution by space one-dimensionalizing the changes in the temperature of the mixed gas which are calculated by the calculation unit 4 using Formulae 3 and 4 that are stored as the computation data 13 in the computation data storage unit 3. Furthermore, the determination unit 5 compares the simulation temperature distribution with the temperature distribution that is included in the experiment data 11 in the experiment data storage unit 1. In a case where, as a result of the comparison, the simulation temperature distribution matches or is within a permitted fluctuation range of the temperature distribution that is included in the experiment data 11, the determination unit 5 determines that the temperature distribution that is included in the experiment data 11 can be derived from the changes in the temperature of the mixed gas which are calculated by the calculation unit 4. Furthermore, in a case where the simulation temperature distribution is not within the permitted fluctuation range of the temperature distribution that is included in the experiment data 11, the determination unit 5 determines that the temperature distribution that is included in the experiment data cannot be derived from the changes in the temperature of the mixed gas (that is, the simulation data) which are calculated by the calculation unit 4.

Furthermore, the octane number determination program 14 causes the CPU 50 to calculate the simulation temperature distribution based on the computation data 13 that is stored in the external storage device 10 or the internal storage device 20 and the calculated changes in the temperature of the mixed gas. Furthermore, the octane number determination program 14 causes the CPU 50 to compare the temperature distribution that is included in the experiment data 11 that is stored in the external storage device 10 or the internal storage device 20 with the simulation temperature distribution. Furthermore, the octane number determination program 14 causes the fuel property determination device A1 to function as the determination unit 5 by causing the fuel property determination device A1 to determine whether or not the temperature distribution that is included in the experiment data can be derived from the calculated changes in the temperature of the mixed gas.

The parameter adjustment unit 6 adjusts the parameters (frequency coefficient and activation energy) that are included in the elementary reaction data 12 that is stored in the elementary reaction data storage unit 2.

Specifically, the parameter adjustment unit 6 adjusts the parameters that are included in the elementary reaction data 12 by increasing or decreasing, by predetermined values, the parameters that are associated with the elementary reaction formulae that are included in the elementary reaction data in a predetermined order.

Furthermore, the octane number determination program 14 causes the fuel property determination device A1 to function as the parameter adjustment unit 6 by causing the CPU 50 to adjust the parameters that are included in the elementary reaction data 12 that is stored in the external storage device 10 or the internal storage device 20.

The control unit 7 performs control of the operation procedure and the like of the experiment data storage unit 1, the elementary reaction data storage unit 2, the computation data storage unit 3, the calculation unit 4, the determination unit 5, and the parameter adjustment unit 6.

Furthermore, in a case where the determination unit 5 determines that the temperature distribution that is included in the experiment data 11 can be derived from the changes in the temperature of the mixed gas which are calculated by the calculation unit 4, the control unit 7 of the fuel property determination device A1 of the present embodiment determines that full chemistry analysis is complete. Furthermore, at that point, the control unit 7 inputs, to the output device 40, the latest changes in the concentration of the intermediate products, changes in the temperature of the mixed gas, and the parameters that are included in the elementary reaction data 12 as analysis results, which are stored in the external storage device 10 or the internal storage device 20.

On the other hand, in a case where the determination unit 5 determines that the temperature distribution that is included in the experiment data cannot be derived from the changes in the temperature of the mixed gas which are calculated by the calculation unit 4, the control unit 7 causes the parameter adjustment unit 6 to adjust the parameters that are included in the elementary reaction data 12. Furthermore, the control unit 7 causes the calculation unit 4 to calculate the changes in the concentration of the intermediate products and the changes in the temperature of the mixed gas once again, and causes the determination unit 5 to determine whether or not the pipe wall temperature distribution that is included in the experiment data 11 can be derived from the calculated changes in the temperature of the mixed gas.

Furthermore, the octane number determination program 14 causes the CPU 50 to function as the control unit 7.

The octane number determination unit 8 calculates the combustion characteristics of a fuel by performing a simulation (for example, CFD analysis) based on the parameter-adjusted elementary reaction data that is obtained by completing full chemistry analysis. Furthermore, the octane number determination unit 8 determines the octane number based on the combustion characteristics of the fuel.

Further, the octane number determination unit 8 of the fuel property determination device A1 of the present embodiment performs a simulation in which the generation states of a cool flame and a hot flame in a case where a premixed gas of a fuel and an oxidant is combusted are calculated as the combustion characteristics of the fuel.

Here, the octane number determination unit 8 of the fuel property determination device A1 of the present embodiment uses a pipe with a diameter that is smaller than the extinguishing diameter that is similar to the pipe 110 that is used in the microflow reactor described above. Furthermore, the octane number determination unit 8 executes the simulation by conferring a temperature gradient to the longitudinal direction with respect to the pipe, and assuming that a premixed gas G, of which the flow amount is set to have a flow speed at which the formation position of the flame is not influenced by the flow speed, is supplied to the pipe. The octane number determination unit 8 then calculates the calorific values of the cool flame and the hot flame, the ratio of the calorific values of the cool flame and the hot flame, and the ignition temperatures of the cool flame and the hot flame as the combustion characteristics of the fuel.

Furthermore, the octane number determination unit 8 determines the octane number of an unknown fuel by comparing the combustion characteristics that are obtained by a simulation in a case where the unknown fuel is used and the combustion characteristics that are obtained by a simulation in a case where the reference fuel is used.

Specifically, the octane number determination unit 8 performs a simulation in a case where a plurality of reference fuels with different mixing ratios of isooctane and n-heptane are used, and calculates the combustion characteristics of each. Further, the octane number determination unit 8 calculates the combustion characteristics of the unknown fuel by performing a simulation in a case where the unknown fuel is used. Furthermore, the octane number determination unit 8 specifies the reference fuel with combustion characteristics that match the unknown fuel. The octane number determination unit 8 then determines the value indicated by the volume ratio of the isooctane that is included in the specified reference fuel as the octane number of the unknown fuel.

Furthermore, the octane number determination program 14 performs a computation using the CPU 50. Further, the octane number determination program 14 determines the octane number based on the combustion characteristics of a fuel by causing the external storage device 10 or the internal storage device 20 to store a temporary computation result. That is, the octane number determination program 14 is a program for causing the CPU 50, the external storage device 10, and the internal storage device 20 to function as the octane number determination unit 8.

Here, in a case where the octane number of the unknown fuel is determined by the octane number determination unit 8, the control unit 7 inputs the octane number into the output device 40. At this time, other than the octane number, the control unit 7 may also input the computation result that is obtained by a simulation that is executed by the octane number determination unit 8 into the output device 40.

Next, a fuel property determination method using the fuel property determination device A1 described above will be described with reference to the flowchart of FIG. 5.

Here, in the fuel property determination method of the present embodiment, the experiment data 11, the elementary reaction data 12, and the computation data 13 are already stored in the experiment data storage unit 1, the elementary reaction data storage unit 2, and the computation data storage unit 3 (the external storage device 10 or the internal storage device 20).

First, under the control of the control unit 7, a reaction mechanism analysis process (step S1) of elucidating an elementary reaction mechanism that represents the combustion reaction of an unknown fuel and an elementary reaction mechanism that represents the combustion reaction of a reference fuel is performed.

Furthermore, in the reaction mechanism analysis process (step S1), an elementary reaction mechanism that composes the chemical reactions between a plurality of types of initial materials including the materials that compose the unknown fuel and the oxidant is analyzed. Furthermore, in the reaction mechanism analysis process (step S1), the analysis result is obtained as an unknown fuel elementary reaction mechanism (fuel elementary reactions in the present invention).

Further, in the reaction mechanism analysis process (step S1), an elementary reaction mechanism that composes the chemical reactions between a plurality of types of initial materials including the materials that compose the reference fuel and the oxidant is analyzed. Furthermore, in the reaction mechanism analysis process (step S1), the analysis result is obtained as a reference fuel elementary reaction mechanism (reference fuel elementary reactions in the present invention). Here, in the present embodiment, two cases of a case in which the combustion reaction of a reference fuel with 100% isooctane is shown and a case in which the combustion reaction of a reference fuel with 100% n-heptane is shown are obtained as the reference fuel elementary reaction mechanism.

Figure 5:
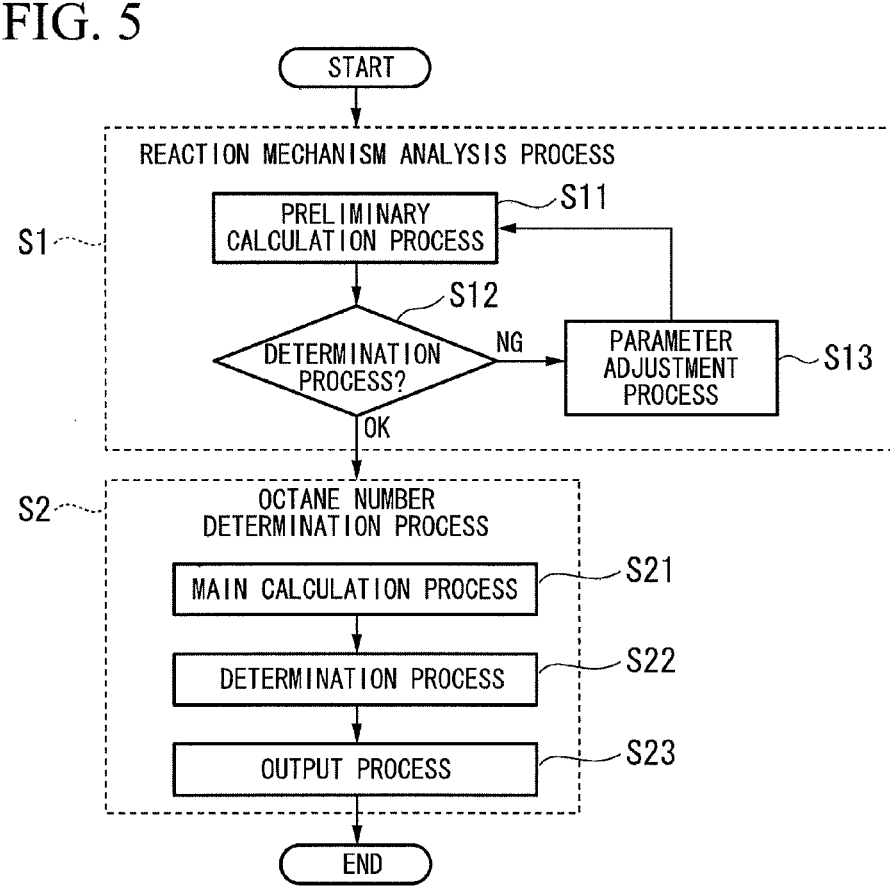
FIG. 5 is a flowchart for describing a fuel property determination method according to the first embodiment of the present invention.

Furthermore, specifically, the elementary reaction mechanism of each fuel is analyzed and obtained by performing a preliminary calculation process (step S11), a determination process (step S12), and a parameter adjustment process (step S13) illustrated in FIG. 5 on each fuel.

To describe in more detail, first, the changes in the concentration of intermediate products and changes in the temperature of a mixed gas (mixed gas in which intermediate products are mixed with uncombusted fuels and the like as described above) in the combustion reaction are calculated by the calculation unit 4 (preliminary calculation process S11).

At this time, the calculation unit 4 calculates the changes in the concentration of the intermediate products and changes in the temperature of the mixed gas using Formulae 1 and 2 that are equations that are time-one-dimensionalized in zero-dimensional space which are stored as the computation data 13 in the computation data storage unit 3, the experiment conditions that are included in the experiment data 11 that is stored in the experiment data storage unit 1, and the elementary reaction data 12 that is stored in the elementary reaction data storage unit 2.

Here, specifically, the changes in the concentration of the intermediate products and changes in the temperature of the mixed gas are calculated by the CPU 50 resolving Formulae 1 and 2 simultaneously with regard to changes in the concentration and changes in the temperature by using the experiment conditions that are included in the experiment data 11 that is stored in the external storage device 10 or the internal storage device 20, the parameters that are included in the elementary reaction data 12, and Formulae 1 and 2 that are included in the computation data 13 that is stored in the external storage device 10 or the internal storage device 20.

Next, under the control of the control unit 7, determination of whether or not the temperature distribution that is included in the experiment data 11 can be derived from the changes in the temperature of the mixed gas which are calculated by the calculation unit 4 is made by the determination unit 5 (determination process S12).

At this time, the determination unit 5 calculates the simulation temperature distribution by space one-dimensionalizing the changes in the temperature of the mixed gas which are calculated by the calculation unit 4 using Formulae 3 and 4 that are stored as the computation data 13 in the computation data storage unit 3. Furthermore, the determination unit 5 compares the simulation temperature distribution with the temperature distribution that is included in the experiment data 11 that is stored in the experiment data storage unit 1. In a case where as a result of the comparison, the simulation temperature distribution matches or is within a permitted fluctuation range of the temperature distribution that is included in the experiment data 11, the determination unit 5 determines that the temperature distribution that is included in the experiment data 11 can be derived from the changes in the temperature of the mixed gas which are calculated by the calculation unit 4. Further, in a case where as a result of the comparison, the simulation temperature distribution is not within a permitted fluctuation range of the temperature distribution that is included in the experiment data 11, the determination unit 5 determines that the temperature distribution that is included in the experiment data 11 cannot be derived from the changes in the temperature of the mixed gas which are calculated by the calculation unit 4.

Specifically, the simulation temperature distribution is calculated by the CPU 50 space one-dimensionalizing the calculated changes in the temperature of the mixed gas using Formulae 3 and 4 that are included in the computation data 13 that is stored in the external storage device 10 or the internal storage device 20. Furthermore, the CPU 50 compares the simulation temperature distribution with the temperature distribution that is included in the experiment data 11 that is stored in the external storage device 10 or the internal storage device 20. Next, the CPU 50 determines whether or not the temperature distribution that is included in the experiment data 11 can be derived from the calculated changes in the temperature of the mixed gas.

In a case where it is determined in the determination process S12 that the temperature distribution that is included in the experiment data 11 cannot be derived from the changes in the temperature of the mixed gas which are calculated in the calculation process S11, the parameters that are included in the elementary reaction data 12 that is stored in the elementary reaction data storage unit 2 are adjusted by the parameter adjustment unit 6 under the control of the control unit 7 (parameter adjustment process S13).

Specifically, the CPU 50 adjusts the parameters that are included in the elementary reaction data 12 that is stored in the external storage device 10 or the internal storage device 20.

Furthermore, when the parameter adjustment process S13 is complete, the calculation process S11 is performed once again.

By repeating the preliminary calculation process (step S11), the determination process (step S12), and the parameter adjustment process (step S13), it is determined in the determination process S12 that the temperature distribution that is included in the experiment data 11 can be derived from the changes in the temperature of the mixed gas which are calculated in the calculation process S11.

In a case where it is determined in the determination process S12 that the temperature distribution that is included in the experiment data 11 can be derived from the changes in the temperature of the mixed gas which are calculated in the calculation process S11, the control unit 7 (CPU 50) determines that full chemistry analysis is complete. Then, an octane number determination process (step S2) as illustrated in FIG. 5 is performed. Here, the octane number determination process corresponds to the property determination process according to the present invention.

Here, as described above, since the preliminary calculation process (step S11), the determination process (step S12), and the parameter adjustment process (step S13) are performed for each fuel, when the octane number determination process (step S2) is performed, all unknown fuel elementary reaction mechanisms and reference fuel elementary reaction mechanisms are already obtained. Furthermore, such unknown fuel elementary reaction mechanisms and reference fuel elementary reaction mechanisms are stored in the external storage device 10 or the internal storage device 20.

Next, the octane number determination process (step S2) is a process of calculating the combustion characteristics of a fuel by performing a simulation based on the elementary reaction mechanism. Furthermore, the octane number determination process (step S2) is a process of determining the octane number of an unknown fuel based on the combustion characteristics of the fuel.

Specifically, in the octane number determination process (step S2), the octane number is determined by performing a main calculation process (step S21), a determination process (step S22), and an output process (step S23) as illustrated in FIG. 5, and the determined value is output.

To describe in more detail, the combustion characteristics of a fuel are calculated through a simulation by the octane number determination unit 8 using the elementary reaction mechanism (main calculation process S21).

For example, the octane number determination unit 8 calculates the calorific values of the cool flame and the hot flame, the ratio of the calorific values of the cool flame and the hot flame, and the ignition temperatures of the cool flame and the hot flame as the combustion characteristics of the fuel by using the reference fuel elementary reaction mechanism.

Figure 6:
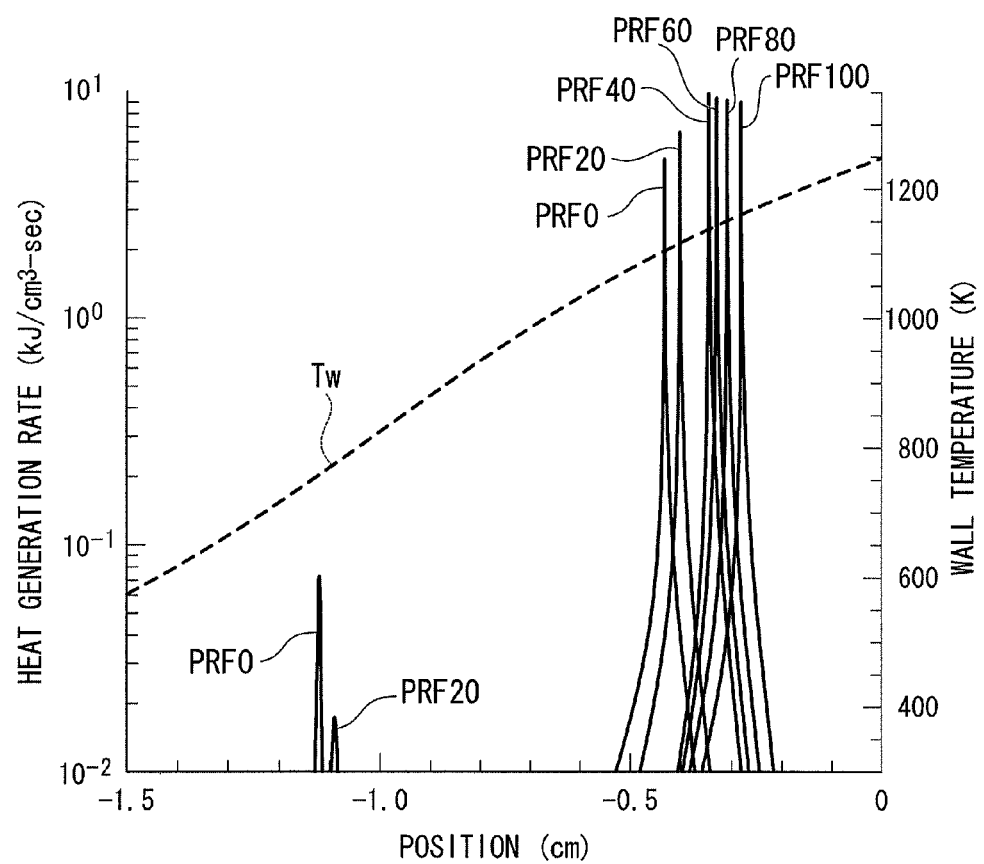
FIG. 6 is a graph that visualizes the result of a simulation using the reference fuel which was performed during the fuel property determination method of the present invention.

FIG. 6 is a diagram in which the octane number determination unit 8 performs a simulation of combustion-reacting the reference fuel, and the simulation result that is obtained as a result is visualized. Here, the combustion characteristics of a reference fuel with an octane number of 0 (PRF 0), the combustion characteristics of a reference fuel with an octane number of 20 (PRF 20), the combustion characteristics of a reference fuel with an octane number of 40 (PRF 40), the combustion characteristics of a reference fuel with an octane number of 60 (PRF 60), the combustion characteristics of a reference fuel with an octane number of 80 (PRF 80), and the combustion characteristics of a reference fuel with an octane number of 100 (PRF 100) are illustrated in FIG. 6. Further, in FIG. 6, Tw represents the pipe wall temperature of the pipe that is used in the simulation (that is, the gas temperature within the pipe). Further, the horizontal axis of FIG. 6 represents the position in the longitudinal direction of the pipe.

Furthermore, the calorific value of the cool flame that is generated when the reference fuel is combustion-reacted is illustrated by each of the areas enclosed by the graphs that are grouped together on the left side of FIG. 6. Further, the calorific value of the hot flame is illustrated by each of the areas enclosed by the graphs that are grouped together on the right side of FIG. 6. That is, for example, the calorific value of the cool flame that is generated when the reference fuel with an octane number of 0 is combustion-reacted is illustrated by the area enclosed by the graph indicated by PRF 0 on the left side of FIG. 6.

Further, the ignition temperature of the cool flame that is generated when the reference fuel is combustion-reacted is represented by the rising positions of the graphs that are grouped together on the left side of FIG. 6. Further, the ignition temperature of the hot flame is represented by the rising positions of the graphs that are grouped together on the right side of FIG. 6.

Here, the environment in which the unknown fuel is actually used is normally a high-pressure environment. However, since the simulation for obtaining FIG. 6 is a simulation that is performed for describing the combustion characteristics, calculation was performed with the pressure condition set as atmospheric pressure. Therefore, no cool flame is generated for the reference fuels with octane numbers of 40 to 100.

However, in a case where a simulation is performed with the same pressure condition as the environment in which the unknown fuel is actually used, a cool flame is generated during the combustion reaction for the reference fuels with octane numbers of 40 to 100, and the combustion characteristics (the calorific values of the cool flame and the hot flame, the ratio of the calorific values of the cool flame and the hot flame, and the ignition temperatures of the cool flame and the hot flame) are calculated.

Furthermore, in FIG. 6, the temperature gradient represented by Tw is set to be the same as the temperature gradient that is conferred on the pipe 110 of the microflow reactor 100 described above. Therefore, Tw is not a straight line.

However, in the simulation that is performed by the octane number determination unit 8, there is no need for the temperature gradient Tw to suit the microflow reactor, and the temperature gradient Tw can be set freely. A simulation result according to the set temperature gradient is therefore obtained.

In such a manner, with the fuel property determination device A1 and the fuel property determination method of the present embodiment, as long as the elementary reaction mechanism can be analyzed, parameters other than the elementary reaction mechanism can be set arbitrarily in the simulation of the octane number determination unit 8.

Therefore, the fuel property determination device A1 and the fuel property determination method of the present embodiment can perform a simulation by easily changing the pressure environment or the temperature of the fuel, that is, the fuel property determination device A1 and the fuel property determination method of the present embodiment can easily calculate a simulation result that is suited to the actual use environment of the unknown fuel.

Returning to FIG. 5, in the main calculation process (step S21), the octane number determination unit 8 calculates the calorific values of the cool flame and the hot flame that are generated when the unknown fuel is combustion-reacted, the ratio of the calorific values of the cool flame and the hot flame, and the ignition temperatures of the cool flame and the hot flame as the combustion characteristics of the fuel using the unknown fuel elementary reaction mechanism.

Here, specifically, the CPU 50 calculates the combustion characteristics of a fuel based on the octane number determination program using the elementary reaction mechanisms that are stored in the external storage device 10 or the internal storage device 20.

Next, the octane number of the unknown fuel is determined (determination process S22) by the octane number determination unit 8 comparing the combustion characteristics of the unknown fuel with the combustion characteristics of the reference fuel which are calculated in the main calculation process S21 under the control of the control unit 7.

At this time, the octane number determination unit 8 compares at least any one of the calorific values of the cool flame and the hot flame, the ratio of the calorific values of the cool flame and the hot flame, and the ignition temperatures of the cool flame and the hot flame between the unknown fuel and the reference fuel. Furthermore, the octane number determination unit 8 specifies the reference fuel with combustion characteristics that match the unknown fuel, and determines the value that represents the volume ratio of isooctane that is included in the specified reference fuel as the octane number of the unknown fuel.

Here, specifically, the octane number of the unknown fuel is determined by the CPU 50 comparing the combustion characteristics that are stored in the external storage device 10 or the internal storage device 20.

Finally, the octane number of the unknown fuel that is determined in the determination process S22 by the octane number determination unit 8 is output under the control of the control unit 7 (output process S23).

Specifically, by the CPU 50 inputting the octane number of the unknown fuel to the output device 40, the octane number of the unknown fuel is visualized and output in the output device 40.

According to the fuel property determination device A1, the fuel property determination method, and the fuel property determination program of the present embodiment described above, the elementary reactions that compose the chemical reactions when the materials that compose the unknown fuel is combusted are analyzed. Furthermore, the combustion characteristics of the unknown fuel are calculated by a simulation being performed based on the analysis result. The octane number is then determined based on the combustion characteristics.

That is, according to the fuel property determination device A1, the fuel property determination method, and the fuel property determination program of the present embodiment, the octane number can be determined without performing an experiment using an internal combustion engine which was performed in the related art when determining the octane number.

Therefore, according to the fuel property determination device A1, the fuel property determination method, and the fuel property determination program of the present embodiment, the octane number of a fuel can be determined more easily.

Further, according to the fuel property determination device A1, the fuel property determination method, and the fuel property determination program according to the present embodiment, during full chemistry analysis, the simulation data is calculated based on equations that are time-one-dimensionalized in zero-dimensional space. The amount of calculation can therefore be reduced.

Further, according to the fuel property determination device A1, the fuel property determination method, and the fuel property determination program of the present embodiment, adjustment of the parameters that are included in the elementary reaction data 12 is performed to match the temperature distribution in one-dimensional space which is not influenced by uncertain variables in the experiment environment which is obtained by the microflow reactor. It is therefore possible to obtain the solution of parameters that can accurately predict the actual combustion reactions without being influenced by uncertain variables in the experiment environment. Accurate full chemistry analysis can therefore be performed.

In such a manner, according to the fuel property determination device A1, the fuel property determination method, and the fuel property determination program of the present embodiment, full chemistry analysis with a light calculation load which is also accurate can be performed.

Further, according to the fuel property determination device A1, the fuel property determination method, and the fuel property determination program according to the present embodiment, similarly to the octane number determination method of the related art, the octane number is determined by comparing the combustion characteristics of an unknown fuel with the combustion characteristics of a reference fuel with a composition that is regulated in advance. The determined octane number can therefore be treated similarly to the octane number obtained with the technique of the related art.

Further, according to the fuel property determination device A1, the fuel property determination method, and the fuel property determination program of the present embodiment, full chemistry analysis not only of the elementary reactions that compose the combustion reactions of an unknown fuel (unknown fuel elementary reaction mechanism) but also the elementary reactions that compose the combustion reactions of the reference fuel (reference fuel elementary reaction mechanism) is performed.

It is therefore possible to more accurately calculate a simulation when determining the octane number, and the octane number of the unknown fuel can be determined more accurately.

However, since the composition of the reference fuel is already known, there may be a case when an elementary reaction mechanism with sufficiently high accuracy is already provided. In such a case, the full chemistry analysis on the reference fuel may be omitted by using the elementary reaction mechanism. In such a case, the experiments by the microflow reactor 100 using the reference fuel may not be performed either.

According to the fuel property determination device A1, the fuel property determination method, and the fuel property determination program of the present embodiment, when comparing the combustion characteristics of the unknown fuel with the combustion characteristics of the reference fuel in order to determine the octane number of the unknown fuel, at least any one of the calorific values of the cool flame and the hot flame, the ratio of the calorific values of the cool flame and the hot flame, and the ignition temperatures of the cool flame and the hot flame of the unknown fuel is compared with that of the reference fuel.

The calorific values of the cool flame and the hot flame, the ratio of the calorific values of the cool flame and the hot flame, and the ignition temperatures of the cool flame and the hot flame all relate to the cool flame that is the main cause of knocking. Therefore by comparing at least any one of the calorific values of the cool flame and the hot flame, the ratio of the calorific values of the cool flame and the hot flame, and the ignition temperatures of the cool flame and the hot flame of the unknown fuel with that of the reference fuel, an octane number with high reliability can be obtained.

(Second Embodiment)

Next, a second embodiment of the present invention will be described. Here, in the description of the second embodiment, description of portions that are similar to the first embodiment will be omitted or simplified.

Figure 7:
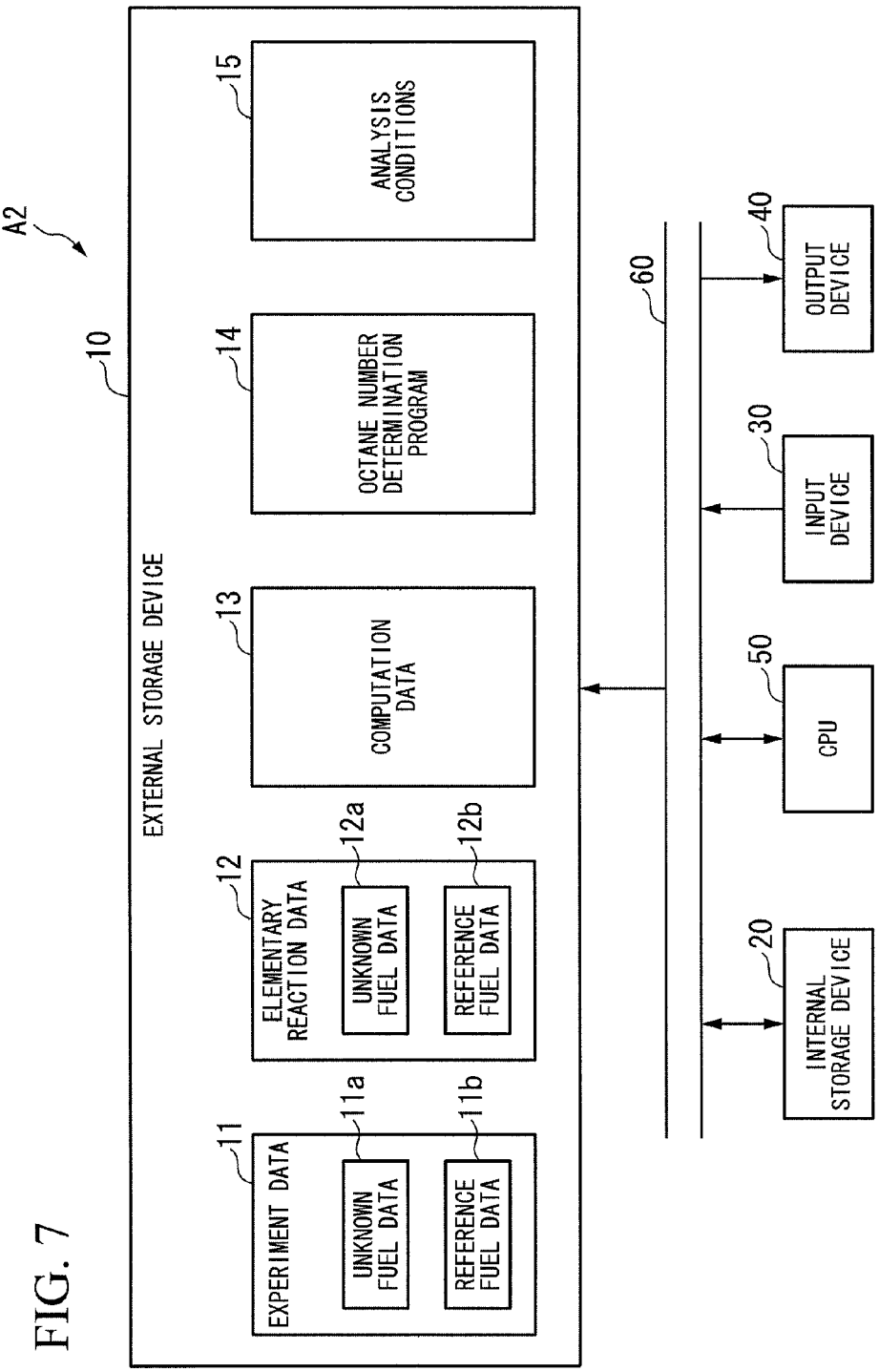
FIG. 7 is a block diagram that illustrates the hardware configuration of a fuel property determination device according to a second embodiment of the present invention.

As illustrated in FIG. 7, a fuel property determination device A2 of the present embodiment has analysis conditions 15 of a simulation that is performed by the octane number determination unit 8 which are stored in the external storage device 10. Here, the analysis conditions referred to here include information such as the amount of calculation that is permitted in the simulation (CFD analysis or the like) that is performed by the octane number determination unit 8 and the types of intermediate products to be analyzed by the simulation.

Figure 8:
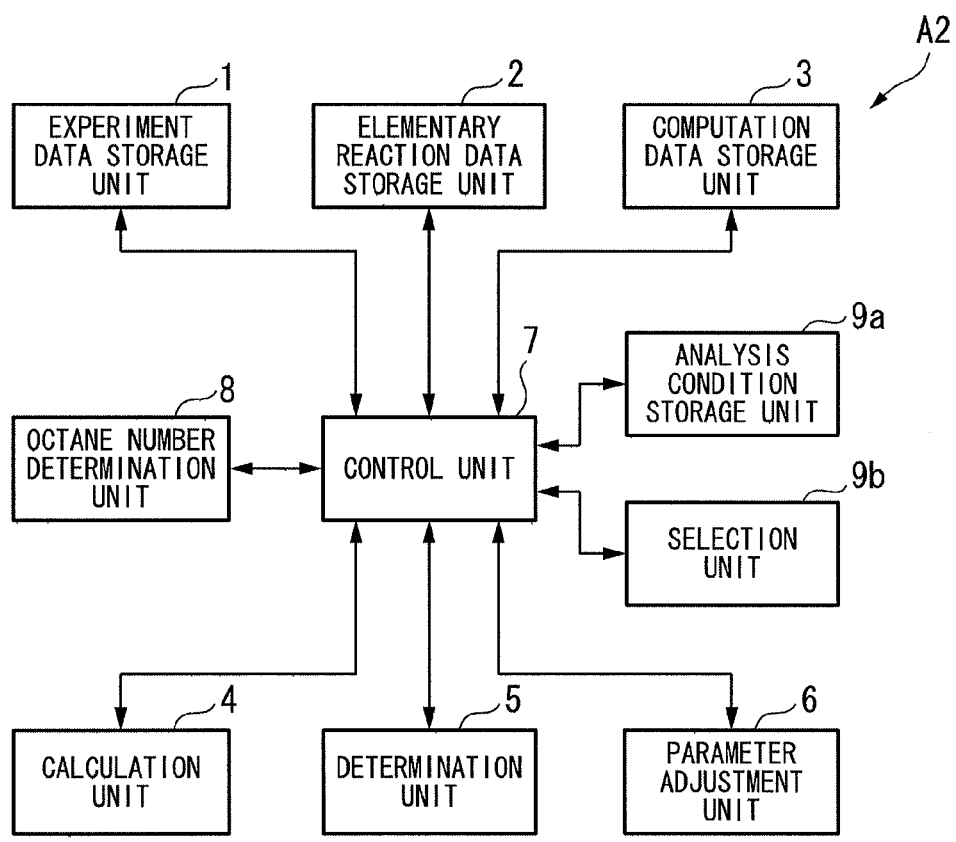
FIG. 8 is a block diagram that illustrates the functional configuration of the fuel property determination device according to the second embodiment of the present invention.

Furthermore, as illustrated in FIG. 8, the octane number determination program 14 causes the fuel property determination device A2 of the present embodiment to function as an analysis condition storage unit 9a and a selection unit 9b.

The analysis condition storage unit 9a stores the analysis conditions 15.

Furthermore, the octane number determination program 14 causes the external storage device 10 that stores the analysis conditions 15 or internal storage device 20 to which the analysis conditions 15 are moved to function as the analysis condition storage unit 9a.

The selection unit 9b is a member that selects a plurality of elementary reaction formulae that describe the chemical reactions based on the analysis conditions 15 and adjusts parameters that are associated with the selected elementary reaction formulae.

Specifically, the selection unit 9b prioritizes and selects the elementary reaction formula to be selected based on the analysis conditions 15 that are stored in the analysis condition storage unit 9a (elementary reaction formula that includes the intermediate products to be analyzed by the simulation by the octane number determination unit 8). Furthermore, the selection unit 9b determines the number of elementary reaction formulae to be selected so as to satisfy the calculation load that is permitted when performing the simulation by the octane number determination unit 8, and performs selection of the elementary reaction formulae based thereon.

Further, the selection unit 9b calculates the simulation temperature distribution once again using only the selected elementary reaction formulae, and compares the simulation temperature distribution with the temperature distribution that is included in the experiment data 11. Furthermore, in a case where the simulation temperature distribution is not within the permitted range of the temperature distribution that is included in the experiment data 11, the selection unit 9b adjusts the parameters relating to the repeatedly selected elementary reaction formulae and repeats the calculation described above until the simulation temperature distribution matches or is within the permitted range of the temperature distribution that is included in the experiment data 11.

Furthermore, the octane number determination program 14 causes the fuel property determination device A2 of the present embodiment to function as the selection unit 9b using the external storage device 10 or the internal storage device 20 and the CPU 50.

Furthermore, in the fuel property determination device A2 of the present embodiment, in a case where it is determined by the determination unit 5 that the temperature distribution that is included in the experiment data 11 can be derived from the simulation temperature distribution, the control unit 7 causes the selection of the elementary reaction formulae and the adjustment of the parameters by the selection unit 9b to be executed.

Figure 9:
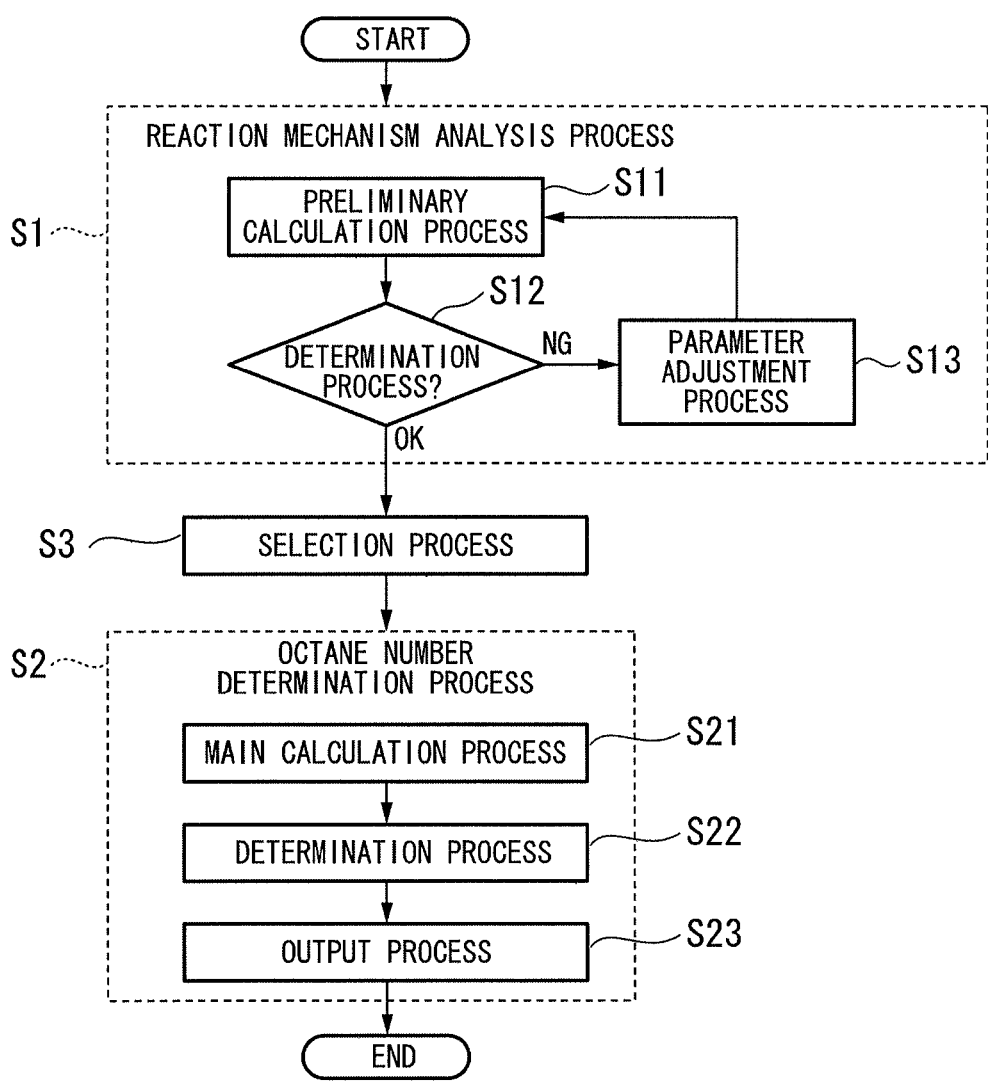
FIG. 9 is a flowchart for describing a fuel property determination method according to the second embodiment of the present invention.

That is, in the reaction mechanism analysis method of the present embodiment, as illustrated in FIG. 9, a selection process S3 of selecting the elementary reaction formulae and performing adjustment of parameters that are associated with the selected elementary reaction formulae is executed between the reaction mechanism analysis process S1 and the octane number determination process S2.

According to the fuel property determination device A2, the fuel property determination method, and the fuel property determination program of the present embodiment, the elementary reaction formulae that are obtained by accurate full chemistry analysis can be optimized for the analysis conditions of the simulation that is performed based on the analyzed elementary reactions.

While preferable embodiments of the present invention have been described above with reference to the attached drawings, needless to say, the present invention is not limited to the embodiments described above. The various shapes, combinations, and the like of each constituent member exemplified in the embodiments described above are only examples, and various modifications based on design requirements and the like are possible without departing from the gist of the present invention.

For example, in the embodiments described above, analysis of the elementary reactions that compose the combustion reaction between a fuel and an oxidant is performed.

However, the present invention is not limited thereto, and the property of a fuel may be determined by analyzing the elementary reactions that compose the chemical reactions between the fuel and another material other than the oxidant.

Further, in the embodiments described above, the temperature distribution that is included in the experiment data 11 is obtained by the microflow reactor 100.

However, the present invention is not limited thereto, and the one-dimensional space temperature distribution may be obtained by another experiment device as long as the device can obtain an accurate one-dimensional space temperature distribution during the combustion reaction.

Further, in the embodiments described above, the temperature distribution of the gas that flows through the inner flow path 111 was used as the one-dimensional space temperature distribution.

However, the present invention is not limited thereto, and for example, in a case where the formation position of the flame satisfies the condition of not being influenced by the flow speed of the premixed gas since the temperature is approximately the same for the gas that flows through the inner flow path 111 and the pipe wall of the pipe 110, the wall face temperature distribution of the pipe 110 (pipe wall temperature distribution) may be used as the one-dimensional space temperature distribution.

Further, while the formation position of the flame trembles in a case where the flow speed of the premixed gas G is fast, the experiment result in such a case may be included in the experiment data 11, and the experiment result may be used in the adjustment of the parameters that are included in the elementary reaction data 12.

Further, in the embodiments described above, the simulation temperature distribution was calculated by one-dimensionalizing the changes in the temperature of the mixed gas which were calculated using equations that are time-one-dimensionalized in zero-dimensional space, and determination was made by comparing the simulation temperature distribution with the temperature distribution that was obtained by the experiment.

However, the present invention is not limited there to, and for example, determination may be made by comparing the temperature distribution that is obtained by the experiment by time-one-dimensionalizing the temperature distribution in zero-dimensional space with the changes in the temperature of the mixed gas which are calculated using equations that are time-one-dimensionalized in zero-dimensional space.

Further, in the embodiments described above, the changes in the concentration of the intermediate products, the changes in the temperature of the mixed gas, and the parameters that are included in the elementary reaction data were output as the analysis result after the analysis was finally completed.

However, the present invention is not limited thereto, and various pieces of data before the analysis is finally completed (for example, parameters that are determined to be of no use in the determination process, and changes in the concentration of the intermediate products, changes in the temperature of the mixed gas, and the like that are based on such parameters) may be output.

Further, in the embodiments described above, the simulation temperature distribution of the mixed gas was calculated from the changes in the temperature of the mixed gas in the inner flow path 111 of the pipe 110, and the temperature distribution of the mixed gas in the inner flow path 111 of the pipe 110 was obtained as the experiment data. Furthermore, the simulation temperature distribution and the temperature distribution as the experiment data were compared, and it was determined whether or not the experiment data could be derived from the simulation data.

However, the present invention is not limited thereto, and whether or not the experiment data can be derived from the simulation data may be determined by calculating the concentration distribution as the simulation data based on the changes in the concentration of the intermediate products in the inner flow path 111 of the pipe 110, obtaining the concentration distribution of the intermediate products in the inner flow path 111 of the pipe 110 as the experiment data, and comparing the concentration distribution that is calculated as the simulation data with the concentration distribution as the experiment data.

Here, the concentration of the intermediate products may be obtained as experiment data by sampling the mixed gas in the inner flow path 111 of the pipe 110 or by performing a measurement by a leaser measurement. Further, the concentration measurement may be performed at any position in the pipe 110. Therefore, for example, in a case where a cool flame and a hot flame are generated, the concentration of the intermediate products from only the cool flame can be measured by performing a concentration measurement at the mid-point between the cool flame and the hot flame.

Further, in the embodiments described above, the experiment data was obtained by performing experiments with the microflow reactor 100 placed at room temperature and in an atmospheric pressure environment.

However, the present invention is not limited thereto, and experiments may be conducted with the microflow reactor 100 placed in an environment closer to the environment in which the unknown fuel is used. As a result, the octane number of the unknown fuel in an actual use environment can be determined more accurately.

Further, in the embodiments described above, full chemistry analysis of the combustion reaction of the reference fuel was performed only for a case of 100% isooctane and 100% n-heptane.

However, the present invention is not limited thereto, and full chemistry analysis may be performed on the combustion reaction of a reference fuel in which isooctane and n-heptane are mixed.

However, in such a case, it is necessary to conduct an experiment in the microflow reactor 100 using a reference fuel that is the target of full chemistry analysis.

Further, in the embodiments described above, calculation was performed using time-one-dimensional equations in zero-dimensional space in order to reduce the calculation load.

However, the present invention is not limited thereto, and as long as the calculation time is permitted, calculations may be performed using other equations. For example, a calculation may be performed using time-one-dimensional equations in three-dimensional space.

Further, in the embodiments described above, the octane number was determined as the property of an unknown fuel.

However, the present invention is not limited thereto, and may be applied in a case where the cetane number is determined as the property of an unknown fuel. Such a case can be realized by replacing the octane number in the embodiments described above with the cetane number.

Further, in the embodiments described above, the experiment data was obtained in a state in which the flame is stable without trembling in the microflow reactor. Furthermore, calculation was also performed with the set condition that the flame does not tremble in the simulation.

However, it is possible to determine the property of an unknown fuel by performing experiments and simulations with the same conditions. Therefore, in the present invention, the experiment data does not necessarily have to be obtained in a state in which the flame is stable without trembling in the microflow reactor. Furthermore, in the present invention, it is also unnecessary to perform calculations by setting the condition that the flame does not tremble in the simulation.

That is, in the present invention, the experiment data may be obtained in a state in which the flame trembles in the microflow reactor. Furthermore, in the present invention, calculations may be performed with the set condition that the flame trembles in simulations as well.

INDUSTRIAL APPLICABILITY

According to the present invention, the property (octane number) of a fuel can be determined more easily.

REFERENCE SIGNS LIST

A1, A2 FUEL PROPERTY ANALYSIS DEVICE
1 EXPERIMENT DATA STORAGE UNIT (EXPERIMENT DATA STORAGE MEANS)
2 ELEMENTARY REACTION DATA STORAGE UNIT (ELEMENTARY REACTION DATA STORAGE MEANS)
3 COMPUTATION DATA STORAGE UNIT (COMPUTATION DATA STORAGE MEANS)
4 CALCULATION UNIT (CALCULATION MEANS)
5 DETERMINATION UNIT (DETERMINATION MEANS)
6 PARAMETER ADJUSTMENT UNIT (PARAMETER ADJUSTMENT MEANS)
7 CONTROL UNIT (CONTROL MEANS)
8 OCTANE NUMBER DETERMINATION UNIT (PROPERTY DETERMINATION MEANS)
14 OCTANE NUMBER DETERMINATION PROGRAM

The invention claimed is:

1. A fuel property determination method of determining a property of an unknown fuel comprising the steps of:
combustion of a mixture of premixed gas and an unknown fuel in a microflow reactor under experimental conditions specified by a flow amount, temperature, and pressure of premixed gas, and the initial concentrations of the unknown fuel and the oxidant;
calculating changes in the concentration of intermediate products and changes in the temperatures of a premixed gas for the unknown fuel and for a reference fuel to obtain an experimental one-dimensional space temperature distribution and a simulated one-dimensional space temperature distribution, respectively, based on an elementary reaction mechanism and the experimental conditions for the unknown fuel and based on an elementary reaction mechanism and experimental conditions for the reference fuel, respectively, the experimental conditions for the reference fuel being specified by a flow amount, temperature, and pressure of premixed gas, and the initial concentrations of the reference fuel and the oxidant;
comparing the experimental one-dimensional space temperature distribution to the simulated one-dimensional space temperature distribution and determining that the experimental one-dimensional space temperature distribution can be derived from the simulated one-dimensional space temperature distribution when the simulated one-dimensional space temperature distribution is within a permitted range of the experimental one-dimensional space temperature distribution; and
obtaining the elementary reaction mechanism for the unknown fuel as a fuel elementary reaction mechanism when it is determined that the experimental one-dimensional space temperature distribution can be derived from the simulated one-dimensional space temperature distribution, calculating combustion characteristics of the unknown fuel by performing a simulation based on the fuel elementary reaction mechanism, and determining a property of the unknown fuel based on the combustion characteristics of the unknown fuel.

2. The fuel property determination method according to claim 1,
wherein the property of the unknown fuel is an octane number, and determining the property of the fuel is an octane number determination process of determining the octane number of the unknown fuel.

3. The fuel property determination method according to claim 2, further comprising the steps of:
a calculation process of calculating simulation data using elementary reaction data including a plurality of elementary reaction formulae that describe the chemical reactions and parameters that are associated with the elementary reaction formulae, and computation data including equations that are time-one-dimensionalized in zero-dimensional space for calculating the simulation data from the elementary reaction data;
a parameter adjustment process of adjusting the parameters that are included in the elementary reaction data, and
the parameter adjustment process and the calculation process using the adjusted parameters are repeatedly performed until it is determined that the experimental one-dimensional space temperature distribution can be derived from the simulated one-dimensional space temperature distribution.

4. The fuel property determination method according to claim 2,
wherein in the octane number determination process, the octane number is determined by comparing the combustion characteristics of the unknown fuel with combustion characteristics of the reference fuel including a composition that is regulated in advance.

5. The fuel property determination method according to claim 4,
wherein elementary reactions that compose chemical reactions between a plurality of types of initial materials including materials that compose the reference fuel are analyzed and obtained as reference fuel elementary reactions, and
in the octane number determination process, the combustion characteristics of the reference fuel are calculated by performing a simulation based on the reference fuel elementary reactions.

6. The fuel property determination method according to claim 2,
wherein in the octane number determination process, the octane number is determined based on at least one of a calorific values of a cool flame and a hot flame that are generated when the unknown fuel is combusted, a ratio of the calorific value of the cool flame and the calorific value of the hot flame that are generated when the unknown fuel is combusted, and ignition temperatures of the cool flame and the hot flame that are generated when the unknown fuel is combusted, which are types of the combustion characteristics of the unknown fuel.

7. A fuel property determination device that determines a property of a fuel, comprising:
- a microflow reactor configured to obtain, by an experiment, an experimental one-dimensional space temperature distribution of a mixture of a gas and the fuel, the experiment involving combustion of the mixture of the gas and the fuel in the microflow reactor;
- reaction mechanism analysis means configured to analyze elementary reactions that compose chemical reactions between a plurality of types of initial materials including materials that compose the fuel and the gas, the chemical reactions including chemical reactions occurring at a time of the combustion of the mixture of the gas and the fuel in the microflow reactor, and obtains the elementary reactions as fuel elementary reactions when it is determined that a simulated one-dimensional space temperature distributor of the mixture of the gas and the fuel, based on the elementary reactions, is within a permitted range of the experimental one-dimensional space temperature distribution of the mixture of the gas and the fuel; and
- property determination means configured to calculate combustion characteristics of the fuel by performing a simulation based on the fuel elementary reactions and determines a property of the fuel based on the combustion characteristics of the fuel.

8. The fuel property determination device according to claim 7,
wherein the reaction mechanism analysis means includes:
- experiment data storage means that stores the experimental one-dimensional space temperature distribution of the mixture of the gas and the fuel;
- elementary reaction data storage means that stores, as elementary reaction data, a plurality of elementary reaction formulae that describe the chemical reactions and parameters that are associated with the elementary reaction formulae;
- computation data storage means that stores, as computation data, equations that are time-one-dimensionalized in zero-dimensional space for calculating simulation data from the elementary reaction data;
- calculation means that calculates the simulation data using the elementary reaction data and the equations that are time-one-dimensionalized in zero-dimensional space;
- determination means that determines whether or not the experimental one-dimensional space temperature distribution of the mixture of the gas and the fuel can be derived from the simulation data;
- parameter adjustment means that adjusts the parameters that are included in the elementary reaction data; and
- control means that repeatedly executes an adjustment of the parameters by the parameter adjustment means and a calculation of the simulation data using the adjusted parameters by the calculation means until the determination means determines that the experimental one-dimensional space temperature distribution of the mixture of the gas and the fuel can be derived from the simulation data.

9. The fuel property determination device according to claim 7,
wherein the property of the fuel is an octane number, and the property determination means is octane number determination means that determines the octane number of the fuel.

10. The fuel property determination device according to claim 9,
wherein the octane number determination means determines the octane number based on at least one of calorific values of a cool flame and a hot flame that are generated when the fuel is combusted, a ratio of the calorific value of the cool flame and the calorific value of the hot flame that are generated when the fuel is combusted, and ignition temperatures of the cool flame and the hot flame that are generated when the fuel is combusted, which are types of the combustion characteristics of the fuel.

11. The fuel property determination device according to claim 9,
wherein the octane number determination determines the octane number by comparing the combustion characteristics of the fuel with combustion characteristics of a reference fuel including a composition that is regulated in advance.

12. The fuel property determination device according to claim 11,
wherein the reaction mechanism analysis means analyzes elementary reactions that compose chemical reactions between a plurality of types of initial materials including materials that compose the reference fuel and obtains the elementary reactions as reference fuel elementary reactions, and
the octane number determination means calculates the combustion characteristics of the reference fuel by performing a simulation based on the reference fuel elementary reactions.

* * * * *